United States Patent [19]
Kückens et al.

[11] Patent Number: 5,667,769
[45] Date of Patent: Sep. 16, 1997

[54] PROCESS AND ARRANGEMENT FOR TREATING HAIR AND THE SKINS OF THE HEAD AND/OR BODY WITH $CO_2$

[75] Inventors: Alexander Kückens, Gross Sarau; Horst Köhl, Bad Oldesloe, both of Germany

[73] Assignee: Technica Entwicklungsgesellschaft mbH & Co. KG, Ratzeburg, Germany

[21] Appl. No.: 185,317

[22] Filed: Jan. 21, 1994

Related U.S. Application Data

[63] Continuation of Ser. No. 886,056, May 18, 1992, abandoned.

[30] Foreign Application Priority Data

| May 24, 1991 | [DE] | Germany | 41 17 023.7 |
| Jul. 25, 1991 | [DE] | Germany | 41 24 728.0 |
| Jan. 10, 1992 | [DE] | Germany | 42 00 467.5 |

[51] Int. Cl.$^6$ ............................................. A61K 7/08
[52] U.S. Cl. .............................. 424/70.1; 424/47; 424/700
[58] Field of Search ............................. 424/70, 71, 40, 424/43, 44–46, 401, 700, 70.4, 70.1; 128/66; 26/DIG. 75

[56] References Cited

U.S. PATENT DOCUMENTS

| 831,941 | 9/1906 | Erlinger | 424/46 |
| 1,958,938 | 5/1934 | Bohandy | 261/19 |
| 4,650,667 | 3/1987 | Eguchi et al. | 424/44 |
| 4,666,707 | 5/1987 | Eguchi | 424/44 |
| 4,726,080 | 2/1988 | Henkin et al. | 128/66 |
| 5,026,551 | 6/1991 | Yorozo et al. | 424/46 |
| 5,132,107 | 7/1992 | Lange | 424/70 |

FOREIGN PATENT DOCUMENTS

| 0155683 | 9/1985 | European Pat. Off. . |
| 0170269 | 2/1986 | European Pat. Off. . |
| 0176694 | 4/1986 | European Pat. Off. . |
| 1491563 | 7/1969 | Germany . |
| 3618726 | 12/1986 | Germany . |
| 3610266 | 10/1987 | Germany . |
| 3840567 | 6/1990 | Germany . |
| 59-141-512-A | 8/1984 | Japan . |

OTHER PUBLICATIONS

Book: Title—Wasser; Author—Karl Holl; published by Walter de Gruyter, Berlin, New York 1979; Cover, title page and pp. 111, 112, 113, 6th Ed.

Book: Title—"Wasser und Wasseruntersuchung"; Author—Leonhard A. Hutter; published by Diesterweg Salle Sauerlander; p. 89;. publication date is unknown but is admitted prior art.

Copy of European Search Report Dated Jun. 9, 1993, for EP 92 10 4086, 3 pages (cover or "Mitteilung," EPO Form 1507 07.90 and 2 pages of citations with English language symbols A, EPO Form 1503 03.82, P.O. 403 and EPO Form P.O. 461) received by German associate on Jun. 14, 1993. No further English translation required per MPEP 609 at pp. 600–667, 68. (Rev. 14, Nov. 1992).

Copenhaver et al. Bailey's Text Book of Histology 1988 pp. 284–292.

Dreisbach Handbook of Poisoning 1971 p. 186.

*Primary Examiner*—Neil S. Levy
*Attorney, Agent, or Firm*—Barnes, Kisselle, Raisch, Choate, Whittemore & Hulbert, P.C.

[57] ABSTRACT

A process and an arrangement for hair care or therapeutic skin treatment are provided which most finely impregnate the heated and running water with $CO_2$ directly before it is contacted with the hair or skin and which serve for lowering the pH value to values markedly below 7 due to the carbonic acid forming proportionately.

13 Claims, 1 Drawing Sheet

PROCESS AND ARRANGEMENT FOR TREATING HAIR AND THE SKINS OF THE HEAD AND/OR BODY WITH CO₂

This is a continuation of application Ser. No. 07/886,056 filed on May 18, 1992, now abd.

As is well known, hair, just like the skins of head and body, are strongly burdened by environmental influences and the preparations and methods used for treatments serving for cleaning, cosmetic, therapeutic or curing purposes. In this case, it is of importance that swelling of the cells or pores of skin or hair or spreading of the dandruffs may be helpful or even necessary with certain treatments. In this case, the dandruffs and pores open so that the aqueous treating substances get a better access and develop improved action. For example, such swelling processes can be favored by alkaline aqueous treating substances. In contrast thereto, acidic preparations reverse this process, i.e. they frequently have smoothing and astringent effects. For example, hair gloss rinsers are acidic, so that the dandruffs fit closely and in addition to the use of fat and gloss substances a uniform dandruff layer, fitting closely, adds to the natural gloss. As is known, various weak acids such a citric acid, tartaric acid and the like serve for acidifying hair gloss agents. The most varying kinds of buffer mixtures are also used for preserving or restoring the protective acid mantle of the skin, e.g. ammonium monohydrogencitrate in combination with anhydrous citric acid in an oil-in-water emulsion or the like.

However, none of these substances can be used or used only after consulting a physician, particularly in the case of skin diseases, open wounds or especially susceptible skin areas.

On the other hand, full, partial or shower baths are known for care or treatment, which along with the most varying acids and trace elements also contain carbon dioxide and carbonic acid. Reference is made in this connection to the natural spring waters of medicinal springs having various compositions, for example. Today, it is well known that the actual therapeutical effect of these medicinal springs is represented by the $CO_2$ or $H_2CO_3$ content and that the other components, differing from one spring to the other, have no serious influence.

Furthermore, bath additives are known for the domestic use, which are usually made of several components, including acid carriers and acid formers from which $CO_2$ gas bubbles escape when inserted in the bath water (cf. in this connection U.S. Pat. No. 4,666,707 or DE-OS 36 18 726, for example). Or the water is impregnated under high pressure with $CO_2$ gas, filled into pressure bottles for sale and then distributed for use in the bath water.

The various bath additive compositions also contain acids such as citric acid or the like and often develop extremely involved synergetic effects with other substances.

The known measures are also relatively expensive. In addition, it is frequently common or necessary to finally rinse or shower with warm or cold water after a corresponding treatment. In many therapeutic, cosmetic, cleaning or caring additives, particularly those having a limited exposure time, such a final rinsing or showering step or the like is absolutely necessary and prescribed.

The object of the present invention is to enable a person to be treated, also a person treating himself, in a simple and cost-saving manner to promote recovery and strengthen the natural stamina of hair and the skins of head and body.

In one embodiment, this problem is solved by a process for hair care in which after a care treatment (washing, dyeing, perming treatment, hair conditioning pack step or the like), the hair is subjected to a hair gloss rinse having acidic and astringent effects, and for hair gloss rinse the optionally warm water taken directly from a conventional pressure source for water (water supply line, flow heater, hot-water tank or the like) is used, to which pure $CO_2$ gas as the only acid former is supplied from a $CO_2$ compressed-gas container at a pressure markedly below the static pressure of the water taken from the pressure source for water at a point of the water flow path at which the static pressure of the water is lowered below the pressure of the $CO_2$ gas, the pH value being adjusted accurately and constantly to a certain value between 5 and 6, particularly 5.2.

In another embodiment, this problem is solved by a process for the caring or therapeutic treatment of the skin, in which the body or part of the body is subjected to a shower or bath after-treatment, at least after a therapeutic or caring or cleaning bath treatment (partial bath, full bath, shower bath or the like), and the skin is subjected to a deswelling or astringent effect by means of the shower or bath after-treatment, and for the purpose the optionally warm water taken directly from a conventional pressure source for water (water supply line, flow heater, hot-water tank or the like) is used, to which pure $CO_2$ gas as the only acid former is supplied from a $CO_2$ compressed-gas container having a pressure markedly below the static pressure of the water taken from the pressure source for water at a point of the water flow path at which the static pressure of the water is lowered below the pressure of the $CO_2$ gas, the pH value being adjusted accurately and constantly to a predetermined value between about 5 and 6.7.

In the preferred embodiment, the process of this invention is carried out by an arrangement comprising a pressure reducer housing and a support for a compressed-gas cartridge, wherein the pressure reducer housing comprises a water pre-chamber having a connection, connectable with the supply line or the like, of predetermined affluent cross-section and a discharge channel, connected with the tapping point, of markedly reduced effluent cross-section as compared to the affluent cross-section; wherein the discharge channel is in constant open flow communication with a compressed-gas chamber through one or more connecting bores, which chamber is connected with a gas pre-chamber; wherein the gas pre-chamber is in free flow communication with one side of a flexible membrane and the water pre-chamber is in free flow communication with the other side thereof, and wherein the membrane acts upon a valve member under predetermined closing pre-tension via an actuation element, which member is assigned to the connection between the gas pre-chamber and the support for the $CO_2$ compressed-gas cartridge, the compressed-gas cartridge engaging into the receiver of the pressure reducer housing in an automatically sealing manner.

The invention is based upon the pressure sources for water, such as the conventional water connection to the supply system, pressurized hot-water tank or flow heater or the like, as usually available in each consulting room such as therapeutic baths, hairdresser's and beauty shops or baths in flats. As a rule, the thus provided water is conditioned for reasons of corrosion protection in such a way that its pH value is within the alkaline range. Thus, every bath, every final rinsing or showering or the like with this water makes the hair, skin of the head, dandruffs or skin cells swell and will leave them in this swollen condition even if cold water is used. In swollen or spread condition the cells and pores retain to an increasing extent residues of dirt particles and treating agents which in the subsequent deswelling are enclosed under the dandruffs and in the pores. Furthermore, the swollen cells or spread dandruffs or other harmful substances or pathogens increase the possibility of penetration.

Here, the teaching according to the invention becomes effective by guaranteeing, especially at home, in a very simple manner and at every point treated that all cells, dandruffs or pores of skin and/or hair are contacted with water, which is acidified to a predetermined lowered pH value and develops an astringent effect, at least in the final rinsing, showering or similar step.

In this case, it is essential that the otherwise common synergetic effects are fully avoided. Thus, no substance compositions are added to the water used herein. In contrast thereto, and except for minor amounts of essential oils and/or odorous substances as described hereinafter, the water is only admixed with $CO_2$ bound in the water in an extremely stable physical manner thereby forming $H_2CO_3$.

It is also essential that only the $CO_2$ and the carbonic acid formed therefrom is used for lowering the pH value and acidifying the water. Contrary to all other acid formers, $CO_2$ and $H_2CO_3$ are in a biologically natural proportion to the hair and body cells, and only these substances can markedly lower the pH value in the interior of the cells, even when the exposure time is as short as 1 to 2 minutes. As a result, the removal or separation of particles not belonging to the skin, such as dirt particles or residues of treating substances from a preceding treatment, may be promoted. The cells are deswollen and astringed. In this way, hair and skin are smoothed in a natural manner. Endogenous, e.g. important water-absorbent substances removed from the pores and cells in the alkaline range, are preserved for the skin when the after-treatment is carried out according to the invention. In addition, there is the bactericidal and bacteriostatic effect of carbonic acid which can even be intensified by the measures of claims 6 and 7. The action of $CO_2$ which is kind to the skin promotes a strong circulation of the skins of head and body. Even in the case of damaged skin, e.g. skin diseases or the like, or open wounds, the after-treatment is not only harmless but also promotes the healing process. This applies to relatively different kinds of skin diseases or damages. All in all, recovery and stamina of hair and skin are promoted considerably.

For a success of the new teaching it is also important that any preliminary or main treatment such as washing, dyeing, perming, exposure to curing agents in the case of hair and skin of the head or such as cleaning, cosmetic or therapeutic bathing in the case of other parts of the body may be followed by a use within the limits of customary final rinsing or showering or another after-treatment step.

It is also important that, independent of the hardness or starting pH value of the water and independent of pressure or flow fluctuations, a pH value lowered to an optimum value is preadjusted which can then automatically be maintained accurately and reliably, without the treating person or person to be treated having to watch or interfere. When the water tap is turned on, the after-treatment effect with the preadjusted pH value fully starts immediately.

A precondition for this is the very accurate and stable $CO_2$ impregnation of the water and the accurate and fully automated $CO_2$ gas dosage. This is rendered possible by means of an arrangement which can easily be attached to any conventional treating or bathing or showering or washing place and any fitting present and common there. Thus, the desired functions are fully incorporated into the normal course of a showering or washing or other treating step.

The respective water quality available (e.g. pH value, carbonate proportion, etc.) can be taken into account by a single preadjustment of a basic value for the $CO_2$ gas proportion. Adjustments made at a later date are usually not necessary.

The optimum pH values for the hair treatment are between 5 and 6, particularly around 5.2 to 5.5, and for the treatment of the body skin between about 6 and 6.7.

The invention is also applicable when in a preliminary or main treatment $CO_2$ has already been added in known manner to the water as one of several active substances. While in this connection the $CO_2$ produces synergetic effects with other substances, only the $CO_2$ and the carbonic acid formed therefrom develop their effect promoting the recovery and stamina of pores, dandruffs, skin particles or the like.

If essential oils or odorous substances and/or silicone oil are used, the $CO_2$ gas may be contacted with these substances at any point along the $CO_2$ gas path from the compressed-gas cartridge to the faster running water. However, it is preferred to already introduce these substances dropwise by manufacture during or before the $CO_2$ gas is filled into the compressed-gas containers or compressed-gas cartridges. The distribution and mixture of these substances with the gas is favored by the gas release during the removal of the $CO_2$ gas.

A sudden lack of odor can in this case be advantageously used as an indication of the fact that the compressed-gas container is empty.

It is useful to chose the essential oils or odorous substances in such a way that they are highly toxic for microorganisms, particularly on account of components such as aldehyde and ketons. These oils include, among other things, thyme oil, eucalyptus oil, caraway oil or the like, all of which have bactericidal effects. Therefore, in addition to the gloss and odorous effect these oils have effects essentially contributing to the health of hair and skin.

As is well known, silicones serve, among other things, as components or bases for ointments, have a stabilizing effect on hair and above all ensure good adhesion of the essential oils on hair and skin. The oils and essential substances proposed also mildly irrigate the skin thereby contributing to the healing effect. A mixture consisting of essential oils and silicone oils is preferred.

BRIEF DESCRIPTION OF THE DRAWINGS

By means of diagrams, the invention is described in more detail below on the basis of several embodiments.

The figures use equal reference numbers for equal parts.

Figure 1:
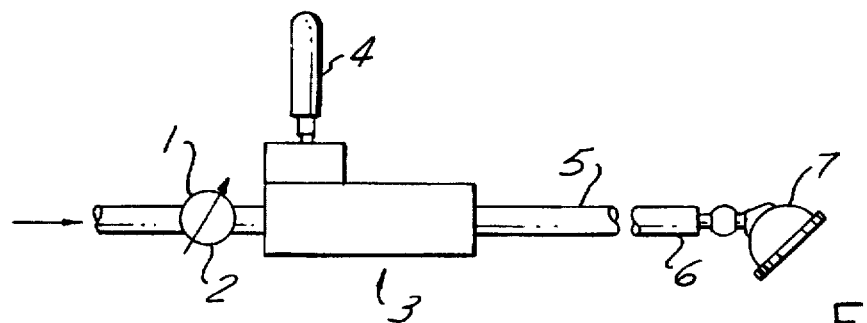
FIG. 1 shows a simplified illustration and side view of a first arrangement for carrying out the new process.

FIG. 1 shows a conduit 1 of predetermined affluent cross-section, which can be connected with a pressure source for water, e.g. a water conduit, flow heater, hot water tank or the like. The water supplied to the affluent cross-section is preferably heated to a temperature between 25° C. and 40° C.

Figure 3:
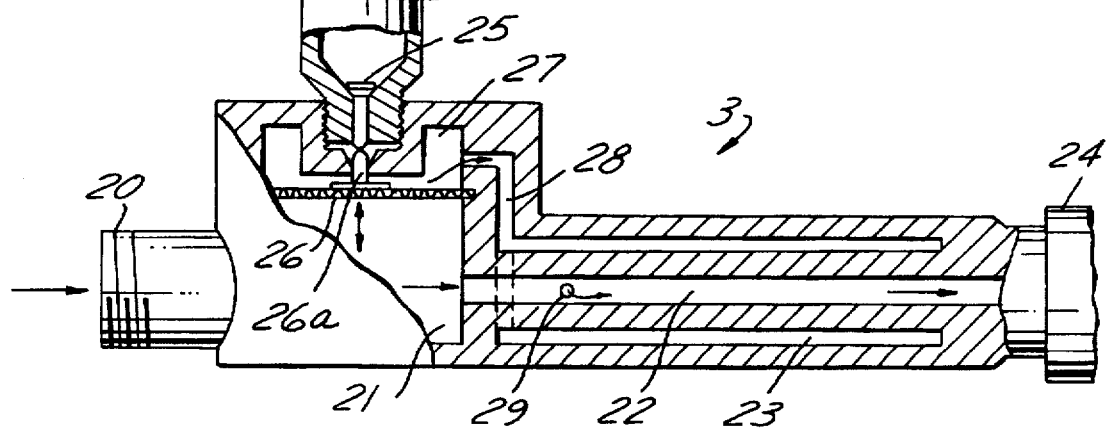
FIG. 3 shows the arrangement at an enlarged scale and partially cut off, by means of which the water can automatically be enriched with the desired $H_2CO_3$ content before it reaches the shower head or another tapping point.

A device 3 is connected to this conduit via an on-off relay valve and shown in more detail in FIG. 3.

According to FIG. 3 the device consists of a block in one end of which a water pre-chamber 21 is provided. This pre-chamber can be connected with valve 2 through a connection 20 having a predetermined affluent cross-section. A discharge channel 22 extends from the water pre-chamber 21, whose cross-section is markedly smaller, preferably about half as large as the affluent cross-section. At its discharge end, the discharge channel 22 opens into a connecting piece 24 which can be connected with a water tap, e.g. a flexible conduit 5 according to FIG. 1, at the end of which an unremovably fitted shower or a detachable shower 6 having a shower head 7 is mounted. The flow cross-sections downstream of the discharge channel 22 are chosen in such a way that they are by no means smaller than the flow cross-section of the discharge channel 22. However, the discharge channel 22 can also open directly into a bathtub or hip-bath.

The discharge channel 22 is surrounded by an annular chamber forming a compressed-gas chamber 23. This compressed-gas chamber 23 is in direct and free flow communication with the discharge channel 22 through at least one bore 29. Furthermore, the compressed-gas chamber 23 communicates with a pre-chamber 27 through a channel 28. The gas pre-chamber 27 is in free flow communication with one side of a flexible membrane 26 and the water pre-chamber 21 is in free flow communication with the other side thereof. The membrane 26 has an actuation element 26a which protrudes through an affluent opening of the housing block and effects on the closing element 25 of the outlet valve, closing at a specified pre-tension, of a compressed-gas cartridge 4 or similar compressed-gas source. In the case of a rinsing hair arrangement, the compressed-gas cartridge may be a cartridge containing 8 or more grams of $CO_2$ gas, for example.

The water flowing in through the affluent cross-section 20 acts on the membrane 26 in the sense of opening the valve 25. The gas flowing out when the valve is open generates a gas pressure in the pre-chamber 27 that counteracts the water pressure applied to the membrane 26. Thus, a predetermined ratio between water pressure and gas pressure adjusts in both pre-chambers automatically and independent of flow rate and water pressure.

The water flows from the water pre-chamber 21 into the narrower discharge channel 22. Due to this, the flow rate increases, e.g. doubles. The static pressure in the discharge channel drops correspondingly, e.g. to about half of the static pressure of the affluent water.

The arrangement is made in such a way that a gas pressure adjusts in the compressed-gas chamber 23 which is higher than the pressure in the effluent cross-section 22, however, lower than the water pressure in the affluent cross-section. This serves for ensuring that the valve 25 closes reliably when the water pressure in the pre-chamber 21 drops below a value necessary for a regular operation.

The water flowing through the discharge channel 22 at a higher rate is admixed with $CO_2$ from the compressed-gas chamber 23 to a minor extent corresponding to the pressure ratio between water and gas and impregnated to such a fine degree that the $CO_2$ gas remains bound over a sufficiently long period of time.

The gas content is adjusted corresponding to the special use. For example, 400 mg of $CO_2$ and more per liter of water are needed for hair rinsing to form sufficient trace amounts of $H_2CO_3$ in the water and lower the pH value markedly below 7. Since the hair rinsing water reaches the hair through the rinsing head or rinsing shower 7 directly after incorporating the $CO_2$ trace amounts, the hair rinsing water has the desired $CO_2$ content and the desired lower pH value when contacted with the hair. The effect on the hair is constant, since the water flowing out is contacted with the hair only for a short period of time and is replaced immediately by the following water.

Figure 2:
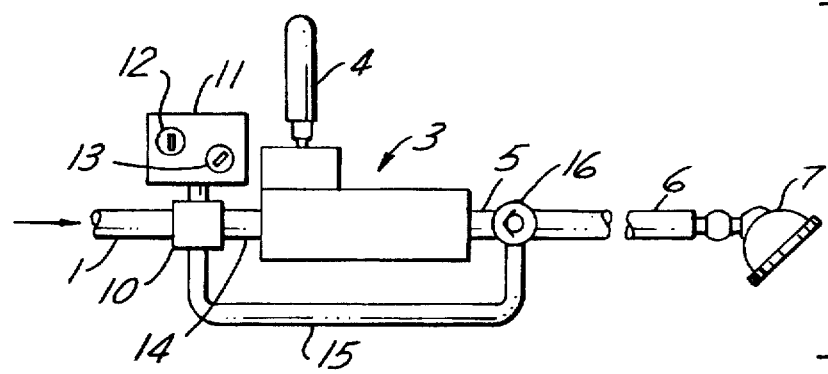
FIG. 2 shows in the same presentation a further developed embodiment of the arrangement for carrying out the process according to claim 6.

Since the hair passes all substances impairing the quality of the hair on to the hair rinsing water enriched with $H_2CO_3$ traces, it may be useful to alternate, at intervals, this form of hair rinsing with a hair rinsing procedure in which untreated hair rinsing water not containing $H_2CO_3$ is used. This may be done by changing the hair rinsing shower. However, the arrangement according to FIG. 2 is useful for this case. In this arrangement a by-pass conduit 15 is provided to the device 3 for the hair rinsing water, which opens downstream of the device 3 and downstream of a check valve 16 assigned to this device into the conduit leading to the shower 7. A reversing valve is provided upstream of the device 3, which alternately connects the device 3 of the by-pass conduit 15 with the supply conduit 1 for the hair rinsing water. The reversal is accomplished by a control means 11, for example, at which the duration and frequency of the intervals can be adjusted by means of corresponding adjusting knobs 12 and 13. An on-off valve may additionally be arranged upstream of the valve arrangement 10. However, this function can also be taken over automatically by the valve means 10 and the corresponding control means 11.

When used for therapeutic purposes, the water heated correspondingly for the bath is most finely impregnated with $CO_2$ gas in the arrangement shown in the figures, so that the water only releases the $CO_2$ gas slowly, e.g. in the case of full baths or hip baths, and remains effective over a prolonged bathing period of 20 to 30 minutes, for example. Here, the water in the arrangement is most finely impregnated with at least about 350 mg of $CO_2$ gas per 1 of water, preferably 500 up to a maximum of 1500 mg/l of water, i.e. essentially without major gas bubbles subjected to a special buoyancy in the water. In many cases, the therapeutical effect increases with increasing $CO_2$ content until about 1250 to 1400 mg/l of water have been reached. A $CO_2$ content exceeding this value does virtually not enhance the effect.

It is useful to heat the water to temperatures between 25° C. and 40° C. before it is fed into the impregnation zone. However, it is also possible to impregnate the water at conventional cold water conduit temperature and then heat it to the desired temperature by means of heated water or to use the cold water without heating at all.

A minor amount of essential odorous substance or oil or silicone oil or a mixture thereof is filled into the compressed-gas cartridge before or during filling it with $CO_2$ gas.

A special advantage is that the measures according to the invention also render possible a bathing or showering temperature reduced by 2–5 degrees, without the person considering this to be cooler or even too cool.

A main advantage of the measures according to the invention consists in that carbonic acid—contrary to all other acids used for treating procedures of this kind—is able to penetrate the cell walls and develope its effects within the cells.

Another advantage of measures according to this invention consists in that the liquefied $CO_2$ promotes the solution and distribution of the minor amounts of essential and/or silicone oil already when introduced into the cartridge.

Experiences show that skin deseases and irritations will be healed definitely by direct skin contact with carbon acid. Hair losses will be reduced respectively avoided because increased blood circulation will improve hair and skin nutrition.

We claim:

1. A method for hair care comprising the steps of:

performing a first hair care step such as washing, showering, dying, perming or conditioning, and then performing a second hair care step by showering said hair with weakly acidified water prepared by:

providing a source of running water at a first water pressure and at a pH in the alkaline range, providing pure $CO_2$ gas at a first gas pressure, reducing said first water pressure to a second water pressure below said gas pressure while confining said water to flow in a confined stream, finely impregnating said water in said confined stream at said reduced water pressure with $CO_2$ gas at said first gas pressure for direct free exchange with said water so that said $CO_2$ gas is bound over in said water in a stable manner as $H_2CO_3$ to weakly acidify said water at a predetermined pH value, and maintaining said predetermined pH value of said weakly acidified water by varying the mount of $CO_2$ gas introduced into said confined stream as a function of said first water pressure to provide said weakly acidified water for showering in said second hair care step.

2. The method of treating human hair which hair has been subjected to swelling when being contacted with water having a pH within an alkaline range such as by washing, showering, dyeing, perming, or conditioning;

wherein weakly acidified water is provided to treat said hair after said hair has been subjected to water having a pH within an alkaline range by the steps of:

providing a source of running water at a first water pressure and at a pH in the alkaline range, providing pure $CO_2$ gas at a gas pressure which is below said first water pressure, reducing said first water pressure to a second water pressure below said gas pressure while confining said water in a walled passageway to flow in a confined stream, introducing said pure $CO_2$ gas under pressure directly into said confined stream of water flowing in said passageway at said second water pressure to finely impregnate said water with $CO_2$ gas for direct free exchange with said water so that said $CO_2$ gas is bound over in said water in a stable manner as $H_2CO_3$ to weakly acidify said water to a pH range between 5 and 6, and then contacting said hair with said weakly acidified water.

3. The method set forth in claim 2 wherein said $CO_2$ gas is provided from a cartridge containing about eight grams of compressed $CO_2$ gas and wherein gas from said cartridge is introduced into said confined stream as a function of variations in said first water pressure to maintain water in said confined stream at a pH range of between 5 and 6.

4. The method set forth in claim 2 wherein said $CO_2$ gas weakly acidifies said water to a pH value of 5.2 to 5.5.

5. The method set forth in claim 2 wherein said first water pressure is subject to variations and wherein $CO_2$ gas is introduced into said confined stream in amounts which vary as a function of said first water pressure variations.

6. The method set forth in claim 2 wherein said hair is contacted With said weakly acidified water immediately after said water is finely impregnated with $CO_2$ gas.

7. The method set forth in claim 6 wherein said hair is contacted with weakly acidified water on a continuously replenished basis by showering water from said confined stream immediately after it has been impregnated with $CO_2$ gas.

8. The method set forth in claim 2 wherein said hair is contacted with said weakly acidified water by a continuous shower of replenished weakly acidified water taken from said confined stream immediately after said $CO_2$ gas is introduced therein.

9. The method set forth in claim 8 further comprising the steps of showering said hair in an alternating sequence of water having a pH within an alkaline range and then said weakly acidified water taken from said confined stream and wherein a last shower in said sequence is with said weakly acidified water.

10. The method set forth in claim 6 wherein $CO_2$ gas is introduced directly into said confined stream of water at a rate of at least of 400 milligrams of $CO_2$ per liter of water.

11. The method set forth in claim 6 wherein said first water pressure is reduced to said second water pressure in a pressure reducing chamber having a water chamber supplied from said source of running water through an inlet passageway having a first cross sectional area, said confined stream flows out of said water chamber through said walled passageway, said walled passageway has a cross sectional area substantially less than said inlet passageway cross-sectional area, said $CO_2$ gas is introduced into said passageway by providing a flexible membrane in said pressure reducing chamber to form said water chamber at one side of said membrane and a gas chamber at the other side of said membrane, establishing fluid communication between said gas chamber and said walled passageway through a third passageway, and wherein $CO_2$ gas is introduced into said confined stream of water by introducing said $CO_2$ gas under pressure into said gas chamber and through said third passageway into said confined stream in said walled passageway and, gas flow into said gas chamber is regulated in accordance with movement of said membrane caused by variations in water pressure in said water chamber to maintain said pH range between the 5 and 6.

12. The method set forth in claim 2 wherein, prior to contacting said hair with said weakly acidified water, water flowing from said source is maintained free of acid formers, other than $CO_2$ and $H_2CO_3$ from being introduced into said weakly acidified water.

13. The method set forth in claim 2 wherein said first water pressure is reduced to said second water pressure by a ratio of about 2:1.

* * * * *